(12) United States Patent
Peters et al.

(10) Patent No.: US 9,066,698 B2
(45) Date of Patent: Jun. 30, 2015

(54) SYSTEMS AND METHODS FOR SAMPLE COLLECTION

(75) Inventors: Scott R. Peters, West Lafayette, IN (US); James M. Hampsch, Lafayette, IN (US)

(73) Assignee: Bioanalytical Systems Inc., West Lafayette, IN (US)

( * ) Notice: Subject to any disclaimer, the term of this patent is extended or adjusted under 35 U.S.C. 154(b) by 854 days.

(21) Appl. No.: 13/270,889

(22) Filed: Oct. 11, 2011

(65) Prior Publication Data
US 2012/0088309 A1 Apr. 12, 2012

Related U.S. Application Data

(60) Provisional application No. 61/391,852, filed on Oct. 11, 2010.

(51) Int. Cl.
| | |
|---|---|
| *G01N 1/28* | (2006.01) |
| *B01L 3/14* | (2006.01) |
| *A61B 5/15* | (2006.01) |
| *B01L 3/02* | (2006.01) |
| *G01N 1/14* | (2006.01) |
| *A61B 5/155* | (2006.01) |

(Continued)

(52) U.S. Cl.
CPC ......... *A61B 5/150503* (2013.01); *Y10T 436/25* (2015.01); *B01L 2200/0689* (2013.01); *B01L 3/0237* (2013.01); *B01L 3/0289* (2013.01); *B01L 3/0296* (2013.01); *B01L 3/021* (2013.01); *B01L 2200/021* (2013.01); *G01N 1/14* (2013.01); *B01L 3/0293* (2013.01); *G01N 35/1016* (2013.01); *A61B 5/15003* (2013.01); *A61B 5/150229* (2013.01); *A61B 5/150358* (2013.01); *A61B 5/155* (2013.01); *A61B 10/0045* (2013.01); *G01N 35/1004* (2013.01); *A61B 5/1427* (2013.01); *A61B 5/150396* (2013.01); *A61B 5/150511* (2013.01)

(58) Field of Classification Search
CPC ............. A61B 10/0045; A61B 5/1427; A61B 5/150396; A61B 5/150503; A61B 5/150511; A61B 5/155; A61B 5/15003; A61B 5/150229; A61B 5/150358; G01N 35/1004; G01N 35/1016; G01N 1/14; B01L 3/021; B01L 3/0237; B01L 3/0289; B01L 3/0293; B01L 3/0296; B01L 2200/021; B01L 2200/0689; Y10T 436/25
See application file for complete search history.

(56) References Cited

U.S. PATENT DOCUMENTS

| | | |
|---|---|---|
| 5,558,834 A | 9/1996 | Chu et al. |
| 5,709,699 A * | 1/1998 | Warner ........................ 606/181 |
| 7,381,204 B2 | 6/2008 | Wilson et al. |

(Continued)

OTHER PUBLICATIONS

Written Opinion of the International Searching Authority, Mailed Mar. 6, 2012.

(Continued)

*Primary Examiner* — Christopher A Hixson
(74) *Attorney, Agent, or Firm* — Ice Miller LLP

(57) ABSTRACT

A tube assembly, system and method for biological sample collection. In one embodiment, the tube assembly of the present disclosure includes a first tube, a second tube, a mechanism for securing the first and second tubes. The securing mechanism orients the first ends of the first and second tubes in a manner such that the first end of the second tube extends beyond the first end of the first tube to create an interstitial space between the outer diameter of the first tube and the inner diameter of the second tube.

15 Claims, 7 Drawing Sheets

(51) Int. Cl.
   *A61B 10/00* (2006.01)
   *G01N 35/10* (2006.01)

(56) References Cited

U.S. PATENT DOCUMENTS

2005/0281713 A1 12/2005 Hampsch et al.
2007/0106234 A1 5/2007 Klein
2008/0275466 A1 11/2008 Skakoon

OTHER PUBLICATIONS

International Search Report, Mailed Mar. 6, 2012.
International Preliminary Report on Patentability, Mailed Apr. 25, 2013.

* cited by examiner

SYSTEMS AND METHODS FOR SAMPLE COLLECTION

CROSS REFERENCE TO RELATED APPLICATIONS

The present U.S. utility patent application is related to and claims the priority benefit to pending U.S. Provisional Patent Application Ser. No. 61/391,852, filed Oct. 11, 2010, the contents of which are hereby incorporated by reference in their entirety into this disclosure.

BACKGROUND

The present disclosure relates generally to the provision of a tube assembly, system, and method for collecting biological fluids, and, more particularly, to a tube assembly, system, and method for biological fluid collection without biological waste fluid or sample dilution.

In the field of health science, there is often a need to collect multiple biological fluid samples (including blood, urine, spinal fluid, synovial fluid, fermentation broth, etc.) from laboratory animals, human subjects, cell cultures, and fermentations. Previously, systems have been designed for the automated collection of biological fluid samples into individual collection vessels. Some of these systems function by moving a new collection vessel below a stationary dispensing needle for each sample collection, whereas other systems function by moving a dispensing needle above a stationary rack of individual collection vessels for each sample collection. Paper or other collection media may be used when drying the sample after collection is desired. In either type of system, the collection vessels are located in close physical proximity to the dispensing needle, and are often supported within a refrigerated environment or located in close physical proximity to the subject.

In cases where it is desired to dispense the biological samples into sealed collection vessels, the dispensing needle in the automated sample collection system is moved down to pierce a septum in the collection vessel. A mechanism is provided to allow displaced air within the sealed collection vessel to escape as the vessel is being filled with the biological fluid sample. After the biological fluid sample is dispensed into the collection vessel, the needle is moved up and out of the collection vessel and the septum reseals the collection vessel. In these automated sample collection systems, the dispensing needle and tubing leading to the dispensing needle are flushed with a rinse solution between every biological fluid sample collection, with the resulting biological fluid waste being flushed out of the end of the dispensing needle.

SUMMARY

The present disclosure comprises a tube assembly, system, and method for collecting undiluted biological samples and the elimination of waste fluid. In an exemplary tube assembly of the present disclosure, the tube assembly comprises a first tube having first and second ends, the first end of the first tube having an opening therein, a second tube having a first end and a second end, the first end of the second tube being open and having a diameter greater than the diameter of the first end of the first tube, and a securing mechanism operable to secure the first tube and the second tube such that the first end of the second tube extends beyond the first end of the first tube, with the first end of the first tube inside the first end of the second tube creating an interstitial space about the first tube at the first end of the second tube.

In an exemplary tube assembly of the present disclosure, wherein when a seal is placed against first end of second tube to form a barrier, a biological sample can pass from the first end of first tube by way of the interstitial space into the opening of the second end of the second tube. In an exemplary tube assembly of the present disclosure, wherein when a seal is placed against second end of second tube to form a barrier a biological sample can pass from the second end of second tube by way of the interstitial space into the opening of the first end of the first tube In an exemplary tube assembly of the present disclosure, the securing mechanism comprises a threaded hub. Further, the threaded hub may be sized and shaped to form a cavity for receipt of a portion of the first tube and the second tube. In an exemplary embodiment of the tube assembly, the securing means further comprises an adhesive within the cavity of the threaded hub to fixedly secure the first tube and second tube.

In an exemplary tube assembly of the present disclosure, the first end of the second tube extends a fixed distance beyond the first end of the first tube, the fixed distance selected from the group consisting of about 0.3 mm to about 1.6 mm, about 0.5 mm to about 1.3 mm, about 0.6mm to about 1.0 mm, and about 0.8 mm.

In an exemplary system for sample collection of the present disclosure, the system comprises a tube assembly having a first tube having first and second ends, the first end of the first tube having an opening therein, a second tube having a first end and a second end, the first end of the second tube being open and having a diameter greater than the diameter of the first end of the first tube, a securing mechanism operable to secure the first tube and the second tube such that the first end of the second tube extends beyond the first end of the first tube, with the first end of the first tube inside the first end of the second tube creating an interstitial space about the first tube at the first end of the second tube, a sample source fluidly coupled to the second end of the first tube, and a collection mechanism comprising a collection medium positioned to receive a fluid from the tube assembly.

In an exemplary system of the present disclosure, the system further comprises a controller coupled to the collection mechanism and the tube assembly, the controller operable to change the time of collection of the fluid or the quantity of the fluid delivered to the collection medium.

In at least one exemplary embodiment of the system of the present disclosure, wherein when a seal is placed against first end of second tube to form a barrier, a biological sample can pass from the first end of first tube by way of the interstitial space into the opening of the second end of the second tube.

In an exemplary tube assembly of the present disclosure, wherein when a seal is placed against first end of second tube to form a barrier, a biological sample can pass from the first end of first tube by way of the interstitial space into the opening of the second end of the second tube.

In an exemplary tube assembly of the present disclosure, wherein when a seal is placed against second end of second tube to form a barrier a biological sample can pass from the second end of second tube by way of the interstitial space into the opening of the first end of the first tube.

In an exemplary tube assembly of the present disclosure, the securing mechanism comprises a threaded hub. Further, the threaded hub may be sized and shaped to form a cavity for receipt of a portion of the first tube and the second tube. In an exemplary embodiment of the tube assembly, the securing means further comprises an adhesive within the cavity of the threaded hub to fixedly secure the first tube and second tube.

In an exemplary tube assembly of the present disclosure, the first end of the second tube extends a fixed distance beyond the first end of the first tube, the fixed distance selected from the group consisting of about 0.3 mm to about 1.6 mm, about 0.5 mm to about 1.3 mm, about 0.6 mm to about 1.0 mm, and about 0.8 mm.

In an exemplary method of sample collection of the present disclosure, the method comprises the steps of introducing a biological sample into a tube assembly of a system of sample collection from a sample source, the system having the tube assembly comprising (1) a first tube having first and second ends, the first end of the first tube having an opening therein (2) a second tube having a first end and a second end, the first end of the second tube being open and having a diameter greater than the diameter of the first end of the first tube, and (3) a securing mechanism operable to secure the first tube and the second tube such that the first end of the second tube extends beyond the first end of the first tube, with the first end of the first tube inside the first end of the second tube creating an interstitial space about the first tube at the first end of the second tube. The system of sample collection used in the exemplary method of the present disclosure also has a sample source fluidly coupled to the second end of the first tube and a collection mechanism comprising a collection medium positioned to receive a fluid from the tube assembly. The exemplary embodiment of the method of sample collection further comprising the step of depositing the biological sample from the tube assembly on the collection media, wherein the biological sample deposited on the collection media is undiluted.

For collection of a biological sample, a tube assembly may be connected to a source of a biological fluid sample through the second end of the first tube. The tube assembly may be placed against an elastomeric seal material to form a seal at the first end of the second tube.

During operation, the biological sample is caused to move into the second end of the first tube through the first tube out the first end of the first tube and into the annulus between the first and second tube. The sample may then be caused to move through the annulus and out the second end of the second tube and into a reservoir. Fluid may then be drawn into the reservoir until adequate volume of undiluted fluid is available for the desired collection volume.

To deliver the sample the fluid lines connecting the second ends of the first and second tubes are closed off by valves. The elastomeric seal material is removed from the first end of the second tube and a collection vial is placed under the tube assemble. The valve between the fluid reservoir and the second end of the second tube is opened and fluid is caused to flow from the reservoir into the second end of the second tube and out the first end of the second and first tube and into the collection vial. The collection vial may be replaced by paper or other collection media if drying of the sample is desired.

In at least one step of the method of collecting an undiluted biological sample, the valve between the reservoir and the second end of the second tube may be closed and the vial removed, the elastomeric seal may then be placed against the first end of the second tube to form a seal. The valves at the second end of the first and second tubes may be opened and the fluid caused to move from the reservoir into the second end of the second tube, through the annulus between the first and second tube, into the first end of the first tube and out the second end of the first tube. A volume of fluid is moved through the tubing assemble such that the remaining biological sample is removed from the tubing assembly and returned to the subject. The connection and flow through the first and second tube may be reversed if desired.

BRIEF DESCRIPTION OF THE DRAWINGS

The features and advantages of the present disclosure, and the manner of attaining them, will be more apparent and better understood by reference to the following descriptions taken in conjunction with the accompanying figures, wherein.

DETAILED DESCRIPTION

Figure 1:
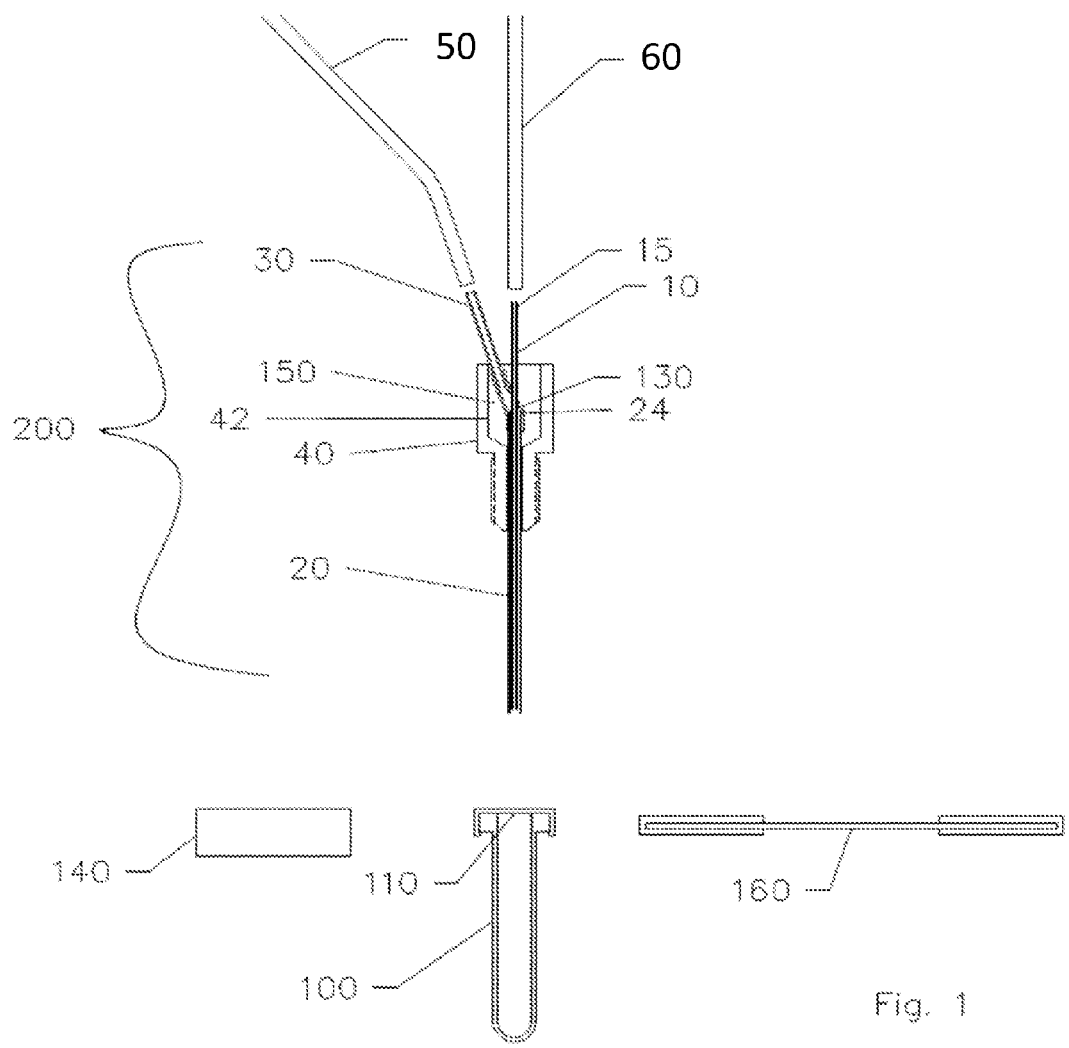
FIG. 1 shows a diagrammatic view of a system for collecting biological samples, according to at least one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Generally, the present disclosure provides a tubing assembly, system, and method for collection of undiluted fluid sampling and elimination of waste fluid. Referring now to FIG. 1, there is shown a diagrammatic view of at least one embodiment of a portion of the system of the present disclosure. Specifically, FIG. 1 shows an embodiment of tube assembly 200 that can be used with an automated sample collection system, as is explained in greater detail herein. Exemplary tube assembly 200 of FIG. 1 is operable to dispense a fluid samples into sealed collection vial 100 or onto collection media 160, such as paper, nitrocellulose, or other materials capable of binding biological samples. Exemplary tube assembly 200 can also be placed against seal material 140 to redirect the flow of the fluid sample. Fluid samples of the present disclosure may in at least one embodiment be a biological sample, such as blood, serum or other blood fractions, semen, saliva, sweat, tears, cerebral spinal fluid, or a combination thereof.

As shown in FIGS. 1-3 and 5, a cross-sectional view of at least one embodiment of the tube assembly 200 of the present disclosure is depicted. In an embodiment of tube assembly 200 of the present disclosure, tube assembly 200 comprises cannula 10 having a first end 12 and second end 15, where first end 12 includes which includes an aperture or opening 13. Exemplary tube assembly 200 further comprises cannula 20 having first end 22 and second end 24. First end 12 of cannula 10 is recessed from first end 22 of cannula 20, and first end 22 of cannula 20 has an inside diameter greater than the diameter of first end 12 of cannula 10. This orientation of cannula 10 and cannula 20 create interstitial space 25 at first end 22 of cannula 20 about cannula 10.

Figure 2:
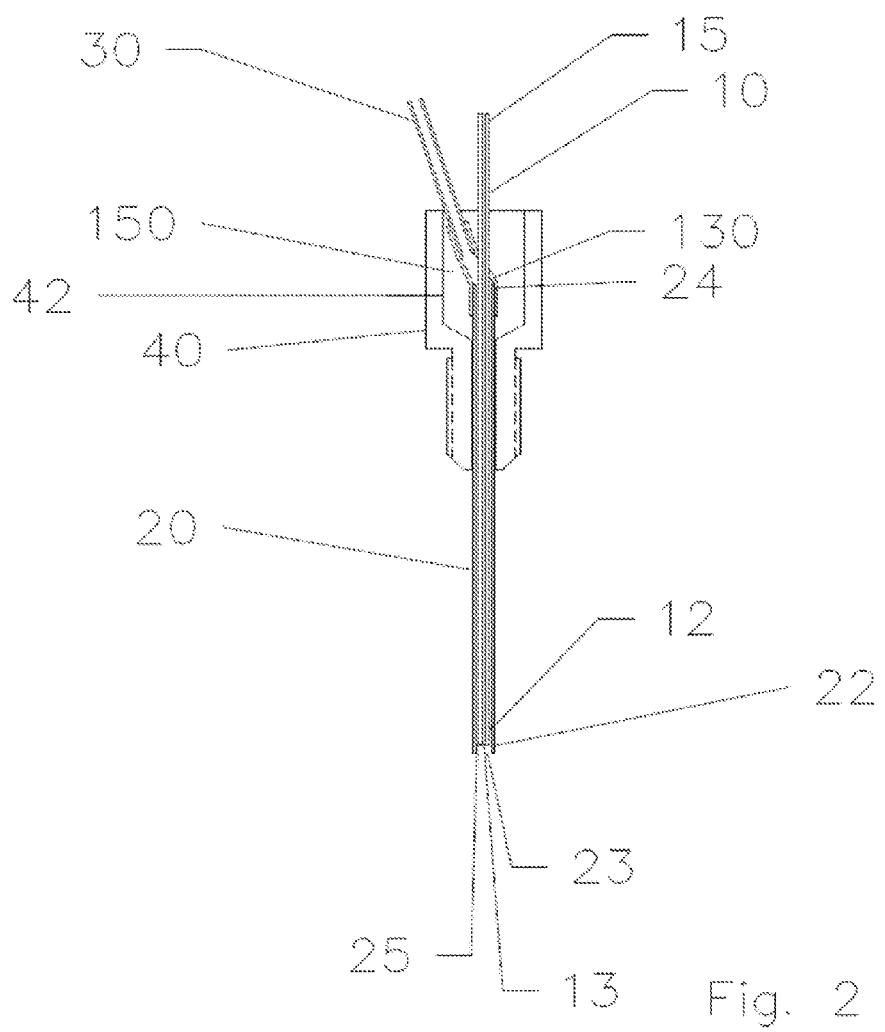
FIG. 2 shows a cross-sectional view of a tube assembly, according to at least one embodiment of the present disclosure.
Figure 3:
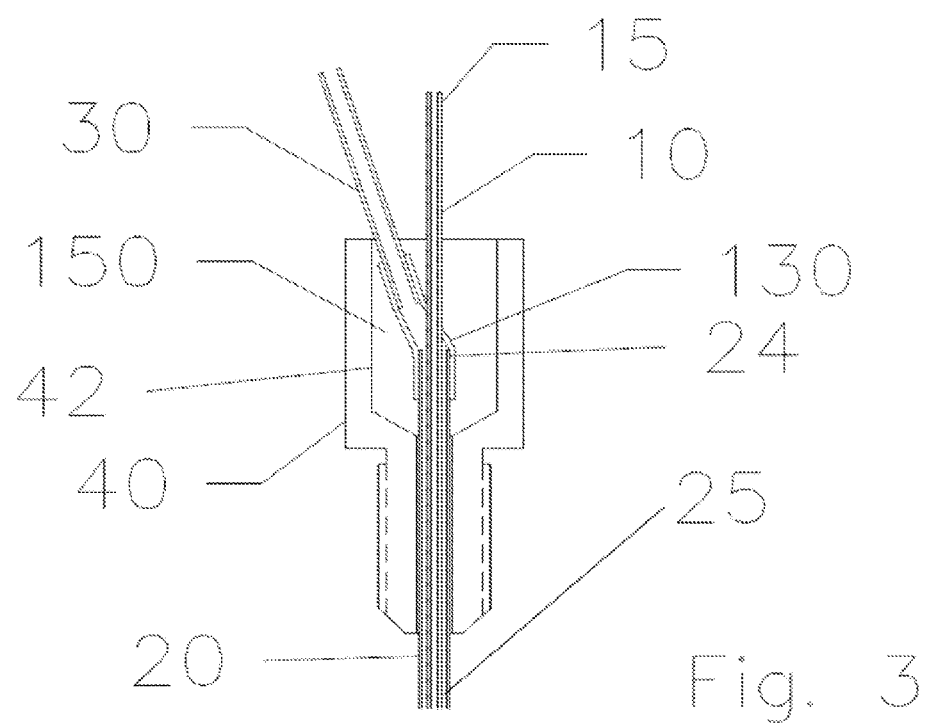
FIG. 3 shows a cross-sectional view of a mechanism for securing the first ends of the first and second tubes, according to at least one embodiment of the present disclosure.

To obtain the aforementioned orientation, exemplary tube assembly 200 of FIGS. 1-3 also includes a securing 39 mechanism for securing cannula 20 to cannula 10. This securing mechanism 39 comprises threaded hub 40 having cavity 42 and adhesive 150 cured within cavity 42. An exemplary adhesive may comprise a silicone, urethane, acrylic, cyanoacrylate, epoxy, as well as various known polymers and co-polymers.

In an embodiment tube 200 of the present disclosure depicted in FIG. 2 and FIG. 3, also shown is short flexible polymer tube 130 press fit over second end 24 of cannula 20. The other end of the flexible polymer tube 130 is press fit over an end of rigid exit tube 30. Cannula 10 passes through a small opening in one sidewall of flexible polymer tube 130 and extends inside the lumen of flexible tube 130, inside the lumen of outer cannula 20, and stopping a short distance before the first end of outer cannula 20. The assembly consisting of flexible tube 130, second end 24 of outer cannula 20, an end of exit tube 30, and a portion of cannula 10 are all placed within cavity 42 of threaded hub 40 and fixed into place by adhesive 150. First end 12 of cannula 10 and first end 22 of outer cannula 20 extend out the bottom of threaded hub 40. Second end 15 of cannula 10 and the distal end of exit tube 30 extend out the top of threaded hub 40.

As previously stated, in the embodiment of FIG. 2 and FIG. 3, cavity 42 is filled with adhesive 150. Adhesive seals all fluid connections and secures all components to threaded hub 40. The combination of threaded hub 40, cavity 42, and adhesive 150 also serve to orient cannula 10 and cannula 20 in the manner shown, and to create interstitial space 25. In this way, a contiguous sealed fluid connection is made from the interstitial space 25 between inner cannula 10 and outer cannula 20 through the flexible tube 130 and through rigid exit tube 30.

It will be appreciated that other mechanisms for securing cannula 10 and cannula 20 to create interstitial space 25 may be used. For example, cannula 10 and cannula 20 may be secured by the material of the threaded hub as the threaded hub is injection molded around the pre-aligned cannula. In addition, it is possible that a single material may comprise cannula 20 and flexible tube 130, and/or exit tube 30. In such an embodiment, cannula 20, flexible tube 130, and exit tube 30 may be comprised of a semi-rigid material, for example, PEEK (polyetheretherketone) tubing.

Based on the illustrations of FIG. 1, FIG. 2, and FIG. 3, it may be simply stated that tube assembly 200 comprises a first tube, a second tube, and a mechanism for securing the first tube to the second tube and create an interstitial space. The first tube comprises cannula 10, the second tube comprises cannula 20, and the securing mechanism comprises threaded hub 40 having cavity 42 therein, with cavity 42 having adhesive 150 cured therein. The securing mechanism secures first end 12 of first tube 10 and first end 22 of second tube 20 such that first end 12 of first tube 10 is recessed from first end 22 of second tube 20, with first end 12 of first tube 10 inside first end 22 of second tube 20 creating interstitial space 25 about first tube 10 at first end 22 of second tube 20.

Figure 5:
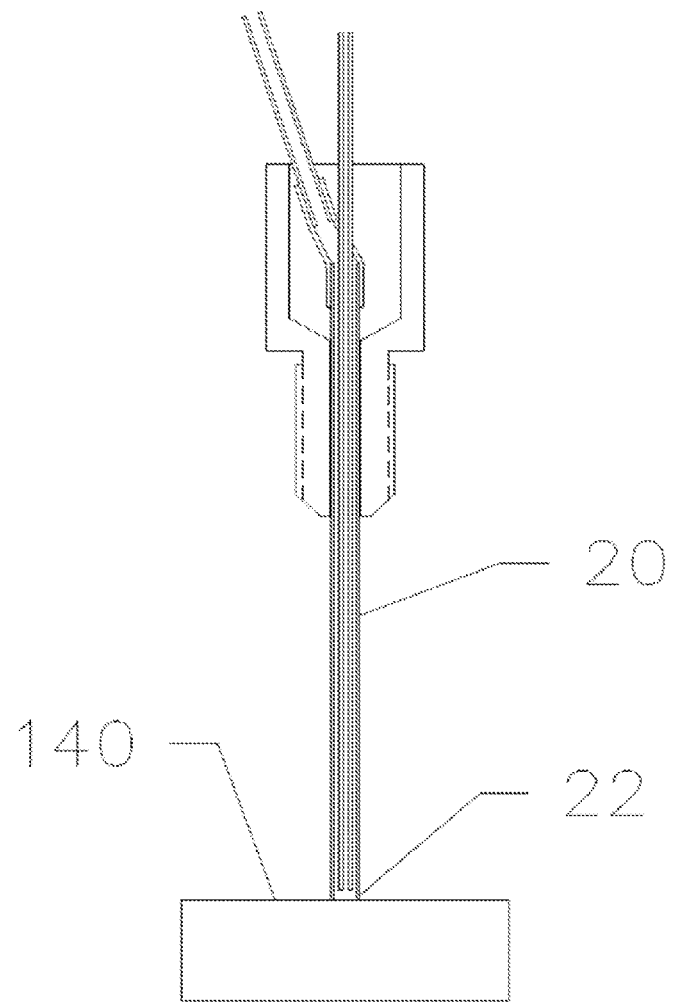
FIG. 5 shows a partial cross-sectional view of a tube assembly in position against an elastomeric seal, according to at least one embodiment of the present disclosure.

This orientation of tube assembly 200 is explained in greater detail in association with the depiction in FIG. 5. FIG. 5 shows a partial cross-sectional view of one embodiment of tube assembly 200 against a sealing material 140. As shown in FIG. 5, the opening of first end 22 of cannula 20 is positioned against seal material 140 such that liquid or air cannot exit or enter the opening of first end 22 of cannula 20.

Referring again to FIG. 1, as previously described, the top of cannula 20 is joined to rigid exit tube 30 that angles away from cannula 10 and cannula 20. The connection formed between cannula 20 and tube 30 is liquid tight so that fluid can pass from cannula 20 to tube 30. Cannula 10, outer cannula 20, and exit tube 30 are all supported within a threaded hub 40 that can be mounted to an automated sample collection instrument as discussed in association with FIG. 4.

Exemplary tubing assembly 200 of the present disclosure includes rigid tube 30 for operable connection to flexible tubing 50. Tubing 50 is operable for connection to the source of the sample fluid (such as a biological fluid) and to the source of a saline solution. This allows a sample fluid to pass through tube 30, tube 130 and the interstitial space between cannula 10 and cannula 20 into collection vial 100 or onto collection media 160.

Figure 6:
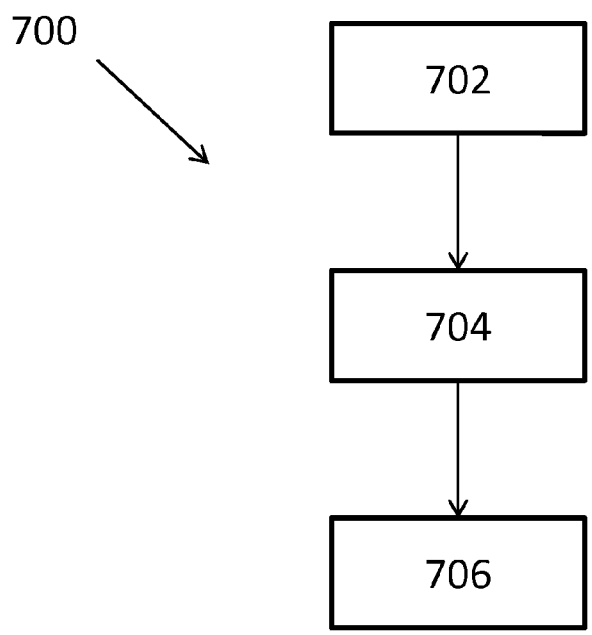
FIG. 6 shows a flowchart of a method of sample collection, according to at least one embodiment of the present disclosure.

Turning to FIG. 6, in at least one embodiment of the method of sample collection 700 of the present disclosure, a fluid sample is taken with tube assembly 200 through tubing 50 operably connected to a source of the sample (not shown). The sample in an exemplary embodiment of method 700 is introduced to tube assembly 200, tubing 50 and tubing set 400 via tubing 60 and catheter 350 while an inlet to tube 200 is sealed with seal 140. Once seal 140 is removed from end 22 of cannula 20 sample collection vessel 100 or collection media 160 is moved under dispensing tube assembly 200 (or tube assembly 200 is moved off of seal 140 and over sample collection vessel 100 or collection media 160) for dispensing of the fluid sample. Dispensing tube assembly 200 may be moved downward relative to sample collection vessel 100 or collection media 160 (or sample collection vessel 100 or collection media 160 is moved upward) to allow first end 22 of cannula 20 pass through a slit in cap 110 so that first end 22 resides within the interior of collection vessel 100 near the top of vial 100 or over collection media 160. The fluid sample can then be delivered into vial 100 (or onto collection media 160) and any air from vial 100 displaced by the introduction of the biological sample into vial 100 escapes out of the slit in cap 110.

Figure 4A:
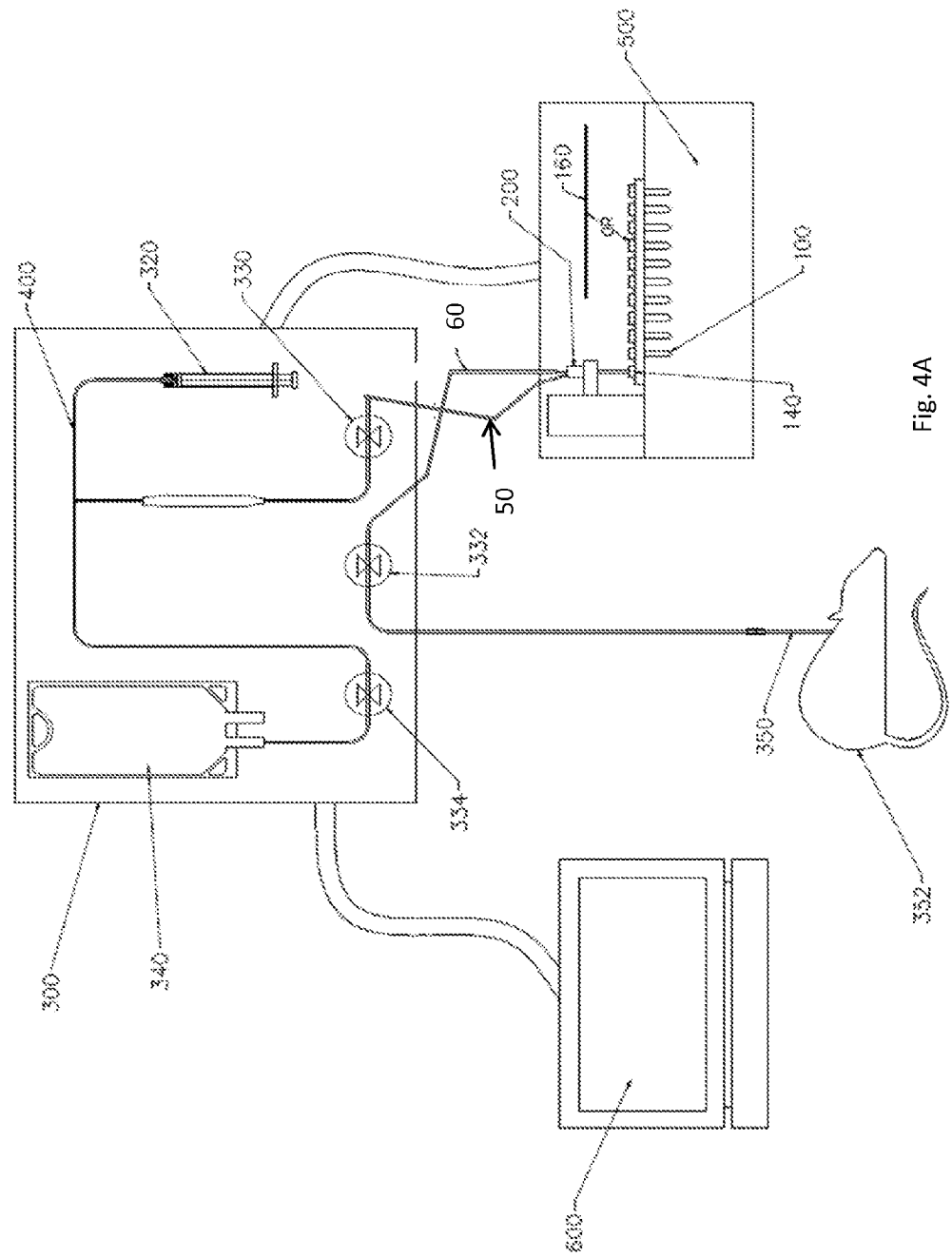
FIGS. 4A and B show diagrammatic views of an automated system, according to at least one embodiment of the present disclosure.

FIGS. 4A and B show diagrammatic views of an embodiment of an automated system according to the present disclosure to:
1. Remove blood from an intravenous catheter implanted in a mammal at programmed intervals;
2. Dispense a portion of the blood into sealed refrigerated (about 3° C.) vials or collection media;
3. Return the remaining blood to the subject; and
4. Return sterile saline to the subject to compensate for the blood removed.

An example of such a blood sampling system is disclosed in U.S. Pat. No. 6,062,224, which is incorporated herein by reference.

An embodiment of an automated blood sampler as depicted in FIG. 4A comprises a control system 300 that incorporates syringe pump 320 for drawing and dispensing the biological sample (such as blood) and saline (rinse solution). First, second, and third pinch valves 330, 332, and 334, respectively, as part of control system 300 are used to direct fluid (sample or saline) to the desired location. Tubing set 400 of control system 300 comprises tubing lines inserted into pinch valves 330, 332, and 334. Tubing set 400 connects a syringe mounted on syringe pump 320, saline reservoir 340, intravenous catheter 350 implanted in subject 352, and an embodiment of a dispensing needle assembly 200 mounted on sample collector 500. sample collector 500 supports collection vials 100 in a refrigerated environment and is operable to move the desired collection vial 100 under dispensing needle assembly 200, and moves needle assembly 200 down to pass through the slit in the cap of collection vial 100. Alternatively the sample collector 500 vial support can be replaced with collection media 160 for dried blood spot collection. In this embodiment, computer 600 is operatively connected to control system 300 and may direct the operation of the instruments, and provides an interface for defining volumes of fluid to sample and collection times of the fluid samples.

Figure 4B:
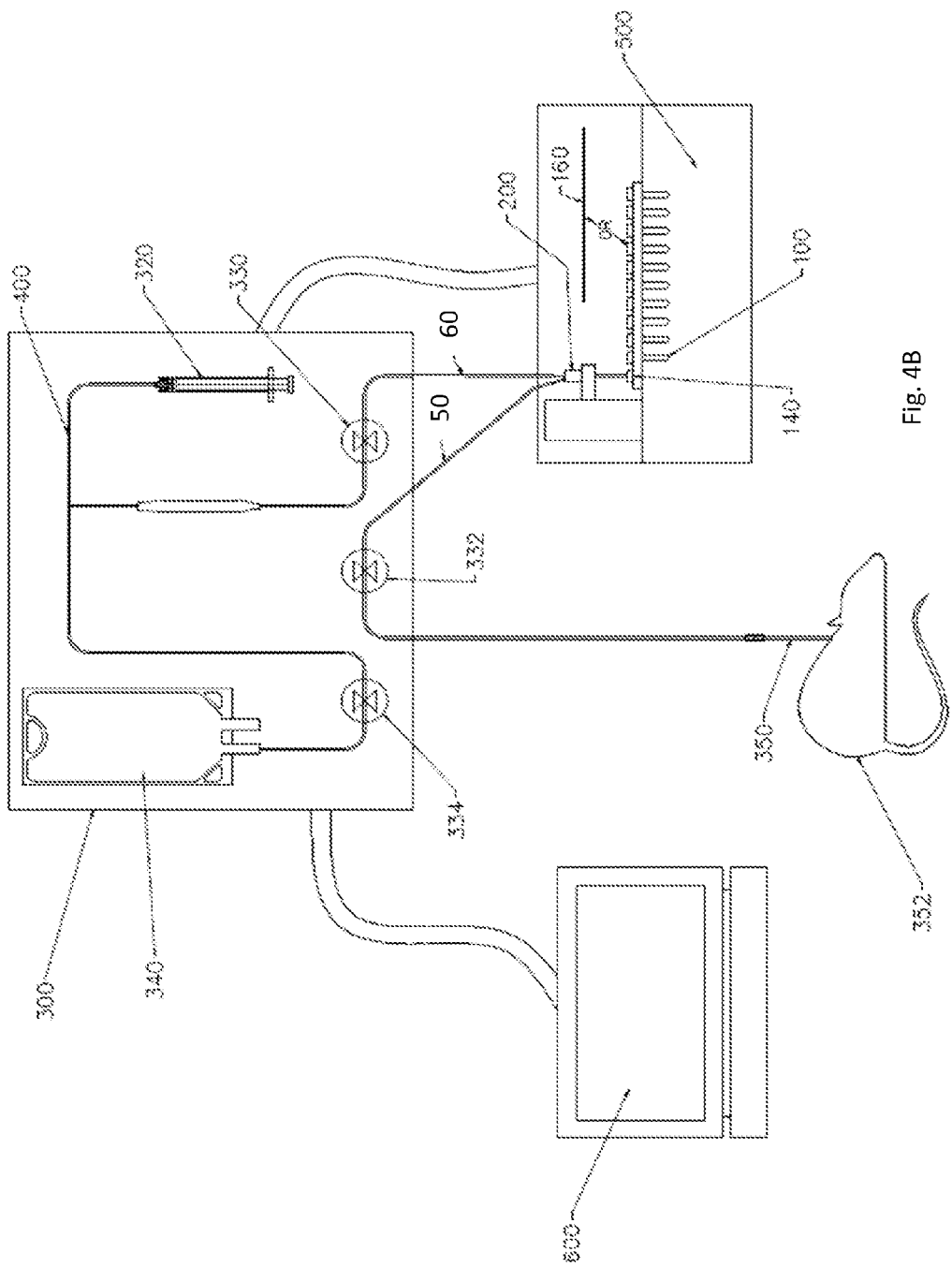

In at least one embodiment of system 650 (as shown in FIG. 4A) of the present disclosure, tube assembly 200 mounted on fraction collector 500, which is connected by tubing 50 to tubing set 400 of control system 300. Flexible tubing 60 connects to second end 15 of cannula 10 of tube assembly 200 and extends through the catheter pinch valve and is connected to catheter 350. Alternately, as shown in FIG. 4B, fraction collector 500 may be connected by tubing 60 to tubing set 400 of control system 300. Flexible tubing 50 connects to second end 15 of cannula 10 of tube assembly 200 and extends through the catheter pinch valve and is connected to catheter 350. Like collection vials 100, elastomeric seal 140 is held in fraction collector 500 alongside collection vials 100 or collection media 160. Fraction collector 500 includes a mechanism for orienting tube assembly 200 with respect to collection vials 100, collection media 160, and elastomeric seal 140. As is well known, such mechanism may comprise robotics or other computationally controlled mechanisms to move tube assembly 200 and/or the rack(s) holding collection vial(s) 100, collection media 160, and elastomeric seal 140.

During operation, a sample of blood may be withdrawn from subject 352 through catheter 350, through line 60, through catheter pinch valve 332 and into second end 15 of cannula 10 of tube assembly 200. The blood exits first end 12 of cannula 10 and enters the interstitial space 25 between cannula 10 and cannula 20 and moves towards the second end 24 of cannula 20. The blood then enters tube 130 and exit tube 30. The blood enters flexible tubing 50 of tubing set 400, through collector pinch valve 300 and into the reservoir of tubing set 400. Blood is drawn until a sufficient quantity is contained in tubing set 400, tubing 50, and tube assembly 200 for the desired sample volume. Dispensing tube assembly 200 is moved upward (or seal 140 is moved downward) and collection vial 100 is moved under tube assembly 200 (or tube assembly 200 is moved over vial 100). Dispensing tube assembly 200 may then be moved downward (or sample collection vessel 100 is moved upward) to allow first end 22 of cannula 20 pass through a slit in cap 110 so that first end 22 resides within the interior of collection vial 100 near the top of vial 100. Movement of the sample initiated by control system 300, into collection vial 100 causes any air from vial 100 to be displaced by the introduction of the biological sample into vial 100 escapes out of the slit in cap 100. Paper or other collection media 160 capable of binding a fluid sample (such as blood) may be used in place of collection vessel 100.

After the sample collection in collection vial 100 is complete, tube assembly 200 is raised by fraction collector 500 (or vial 100 is moved downward) out of collection vial 100, and moved over elastomeric seal 140, and moved downward (or collection vial 100 is moved upward) to seal first end of cannula 20.

As described in U.S. Pat. No. 6,062,224, rinse solution, saline, may be caused to move from saline reservoir through tubing set 400. The connection of tubing set 400 to tubing 50 causes saline to wash the inside of tubing 50 the inside of tube 30 the inside of tube 130 and the interstitial space 25 and the elastomeric seal 140 at opening 23 of cannula 20. The saline then moves through the inside of cannula 10 and through line 60 and through catheter 350 and into subject 352. Sufficient quantity of saline is moved to remove remaining blood and to replace the volume of blood sampled with saline.

In the operation described for the system of FIG. 4, the orienting mechanism of fraction collector 500 moves tube assembly 200. It will be appreciated by those of skill in the art that the orienting mechanism may move tube assembly 200 and/or vials 100, media 160 and seal 140 and be within the scope of the disclosure. In essence, the orienting mechanism must be capable of placing opening 23 of cannula 20 onto seal 140, inserting opening 23 of cannula 20 through cap 110 into the interior of the vial or over collection media 160.

It will be appreciated by those of skill in the art that the present disclosure allows for cleaning of all fluid paths that come in contact with biological fluid. The fluid path and sealing surface may be washed without the need of collection and disposal of rinse solution\biological fluid mix. Furthermore the loss of biological sample associated with traditional dispense needle rinsing has been eliminated.

Various exemplary embodiments of the tube assembly 200 of the present disclosure allow for delivery of undiluted biological samples without loss of additional biological fluid due to purging fluid from the delivery needle prior to and after sample delivery. Further, the elimination of residual biological fluid and rinse solution from the sampling process in various embodiments of the present disclosure eliminates the need to collect, handle and dispose of hazardous waste if the residual biological fluid is hazardous due to the presence of radioisotopes, infectious agents, pathogens, or other risks.

While various embodiments of systems for collecting samples and methods for using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A system for sample collection, the system comprising:
a tube assembly comprising:
a first tube having first and second ends, the first end of the first tube having an outer diameter and having a first tube opening therein;
a second tube having a first end and a second end, the first end of the second tube having a second tube opening therein and the second end of the second tube having a third tube opening therein, the second tube opening having an inner diameter greater than the outer diameter of the first end of the first tube;
a securing mechanism operable to secure the first tube and the second tube such that the first end of the second tube extends beyond the first end of the first tube, with the first end of the first tube inside the first end of the second tube creating an interstitial space about the first tube at the first end of the second tube; and
a seal, wherein when the seal is disposed against the first end of the second tube to form a barrier, wherein a biological sample can pass from the first end of the first tube by way of the interstitial space into the third tube opening of the second end of the second tube;

a sample source fluidly coupled to the second end of the first tube; and a collection vessel comprising a collection medium, wherein the collection medium is capable of binding biological samples, and wherein the collection vessel is positioned to receive a fluid from the tube assembly.

2. The system of claim 1, further comprising a controller coupled to the collection vessel and the tube assembly, the controller operable to change the time of receipt of the fluid or the quantity of the fluid received.

3. The system of claim 1, wherein the collection medium comprises a nitrocellulose material.

4. The system of claim 1, wherein when the seal is disposed against the first end of the second tube to form a barrier, wherein a biological sample can pass from the second end of the second tube by way of the interstitial space into the first tube opening of the first end of the first tube.

5. The system of claim 1, wherein the securing mechanism comprises a threaded hub.

6. The system of claim 5, wherein the threaded hub is sized and shaped to form a cavity for receipt of a portion of the first tube and the second tube.

7. The system of claim 6, wherein the securing mechanism further comprises an adhesive within the cavity of the threaded hub to fixedly secure the first tube and second tube.

8. The system of claim 5, wherein the first end of the second tube extends a fixed distance beyond the first end of the first tube, the distance selected from the group consisting of about 0.3 mm to about 1.6 mm, about 0.5 mm to about 1.3 mm, about 0.6 mm to about 1.0 mm, and about 0.8 mm.

9. A method of sample collection, the method comprising the steps of:

introducing a biological sample into a tube assembly of a system of sample collection from a sample source, the system comprising:

the tube assembly comprising:

a first tube having first and second ends, the first end of the first tube having an outer diameter and having a first tube opening therein;

a second tube having a first end and a second end, the first end of the second tube having a second tube opening therein and the second end of the second tube having a third tube opening therein, the second tube opening having an inner diameter greater than the outer diameter of the first end of the first tube;

a securing mechanism operable to secure the first tube and the second tube such that the first end of the second tube extends beyond the first end of the first tube, with the first end of the first tube inside the first end of the second tube creating an interstitial space about the first tube at the first end of the second tube;

a seal, wherein when the seal is disposed against the first end of the second tube to form a barrier, wherein a biological sample can pass from the first end of the first tube by way of the interstitial space into the third tube opening of the second end of the second tube;

the sample source fluidly coupled to the second end of the first tube; and a collection vessel comprising a collection medium, wherein the collection medium is capable of binding biological samples, and wherein the collection vessel is positioned to receive a fluid from the tube assembly; and depositing the biological sample from the tube assembly on the collection media;

wherein the biological sample deposited on the collection media is undiluted.

10. The method of claim 9, wherein the collection medium comprises a nitrocellulose material.

11. The method of claim 9, wherein the securing mechanism comprises a threaded hub.

12. The method of claim 11, wherein the threaded hub is sized and shaped to form a cavity for receipt of a portion of the first tube and the second tube.

13. The method of claim 11, wherein the securing mechanism further comprises an adhesive within the cavity of the threaded hub to fixedly secure the first tube and second tube.

14. The method of claim 9, wherein the first end of the second tube extends a fixed distance beyond the first end of the first tube, the distance selected from the group consisting of about 0.3 mm to about 1.6 mm, about 0.5 mm to about 1.3 mm, about 0.6 mm to about 1.0 mm, and about 0.8 mm.

15. The system of claim 1, wherein the seal comprises an elastomeric seal material.

* * * * *